(12) United States Patent
Willard et al.

(10) Patent No.: US 11,557,396 B2
(45) Date of Patent: Jan. 17, 2023

(54) ELECTRONIC MEDICAL RECORD EXCHANGE

(71) Applicant: Humana Inc., Louisville, KY (US)

(72) Inventors: Marc Willard, San Jose, CA (US);
James Gough, Los Gatos, CA (US);
Pranay Varma, San Jose, CA (US);
Rahul Somasunderam, Fremont, CA (US)

(73) Assignee: Humana Inc., Louisville, KY (US)

( * ) Notice: Subject to any disclaimer, the term of this patent is extended or adjusted under 35 U.S.C. 154(b) by 398 days.

(21) Appl. No.: 16/817,156

(22) Filed: Mar. 12, 2020

(65) Prior Publication Data

US 2020/0211138 A1    Jul. 2, 2020

Related U.S. Application Data

(63) Continuation of application No. 12/893,384, filed on Sep. 29, 2010, now abandoned.

(51) Int. Cl.
*G16H 40/67*   (2018.01)
*G16H 10/60*   (2018.01)

(52) U.S. Cl.
CPC ............ *G16H 40/67* (2018.01); *G16H 10/60* (2018.01)

(58) Field of Classification Search
CPC ............................ G16H 40/67; G16H 10/60
See application file for complete search history.

(56) References Cited

U.S. PATENT DOCUMENTS

| | | | |
|---|---|---|---|
| 5,664,109 | A | 9/1997 | Johnson et al. |
| 5,729,734 | A | 3/1998 | Parker et al. |
| 5,784,635 | A | 7/1998 | McCallum |
| 7,260,480 | B1 | 8/2007 | Brown et al. |
| 7,408,439 | B2 | 8/2008 | Wang et al. |
| 7,743,065 | B2 | 6/2010 | Yeap et al. |
| 8,249,895 | B2 | 8/2012 | Faulkner et al. |
| 8,805,703 | B2 | 8/2014 | Martin et al. |
| 2002/0046346 | A1 | 4/2002 | Evans |
| 2002/0072911 | A1 | 6/2002 | Kilgore et al. |
| 2002/0116227 | A1 | 8/2002 | Dick |

(Continued)

OTHER PUBLICATIONS

Appeal Briefing Documents and Board Decision for Appeal No. 2020-002983 for U.S. Appl. No. 12/893,384.

*Primary Examiner* — Eliza A Lam
(74) *Attorney, Agent, or Firm* — Standley Law Group, LLP; Jeffrey Standley; Adam Smith

(57) ABSTRACT

Systems and methods providing compatibility between legacy electronic medical record (EMR) systems are disclosed. A first appliance is in two-way electronic communication with a first legacy EMR system and is configured to covert medical records data between a first format utilized by the first legacy EMR system and a common format. A second appliance is in two-way electronic communication with a second legacy EMR system and is configured to convert medical records data between a second format utilized by the second legacy EMR system and the common format. A common appliance is in two-way electronic communication with the first appliance, the second appliance and a third legacy EMR system. The common appliance is configured to convert medical records data between a third format utilized by the third legacy EMR system and the common format.

9 Claims, 5 Drawing Sheets

(56) References Cited

U.S. PATENT DOCUMENTS

| | | |
|---|---|---|
| 2003/0065653 A1 | 4/2003 | Overton et al. |
| 2003/0191669 A1 | 10/2003 | Fitzgerald et al. |
| 2005/0086527 A1 | 4/2005 | Jackson |
| 2005/0159983 A1 | 7/2005 | Sullivan |
| 2005/0187794 A1 | 8/2005 | Kimak |
| 2005/0222876 A1 | 10/2005 | Iwayama et al. |
| 2006/0106644 A1 | 5/2006 | Koo et al. |
| 2006/0106645 A1 | 5/2006 | Bergelson et al. |
| 2006/0122865 A1 | 6/2006 | Preiss et al. |
| 2006/0155581 A1 | 7/2006 | Eisenberger et al. |
| 2006/0261145 A1 | 11/2006 | Robertson et al. |
| 2006/0277076 A1 | 12/2006 | Hasan et al. |
| 2007/0055552 A1 | 3/2007 | St. Clair et al. |
| 2007/0083403 A1 | 4/2007 | Baldwin et al. |
| 2008/0004904 A1* | 1/2008 | Tran ............... A61B 5/411 340/286.07 |
| 2008/0046292 A1 | 2/2008 | Myers et al. |
| 2008/0140855 A1 | 6/2008 | Wallberg |
| 2008/0154642 A1 | 6/2008 | Marble et al. |
| 2008/0177576 A1 | 7/2008 | Jennings et al. |
| 2008/0235358 A1 | 9/2008 | Moribe et al. |
| 2009/0070136 A1 | 3/2009 | Morita et al. |
| 2009/0080408 A1 | 3/2009 | Natoli et al. |
| 2009/0254375 A1 | 10/2009 | Martinez et al. |
| 2010/0094650 A1 | 4/2010 | Tran et al. |
| 2010/0114607 A1 | 5/2010 | Kress et al. |
| 2010/0131293 A1 | 5/2010 | Linthicum et al. |
| 2010/0131299 A1 | 5/2010 | Hasan et al. |
| 2010/0228721 A1 | 9/2010 | Mok et al. |
| 2010/0299155 A1 | 11/2010 | Findlay et al. |
| 2011/0001605 A1 | 1/2011 | Kiani et al. |
| 2011/0119088 A1 | 5/2011 | Gunn |
| 2011/0301977 A1 | 12/2011 | Belcher et al. |
| 2012/0078664 A1 | 3/2012 | Hasan et al. |
| 2012/0101849 A1 | 4/2012 | Mathur et al. |
| 2012/0203571 A1 | 8/2012 | Crapo et al. |
| 2012/0254320 A1 | 10/2012 | Dove et al. |
| 2012/0331567 A1 | 12/2012 | Shelton |
| 2013/0014278 A1 | 1/2013 | Jin et al. |
| 2013/0197940 A1 | 8/2013 | Garber |
| 2013/0282397 A1 | 10/2013 | Easterhaus et al. |
| 2013/0325505 A1 | 12/2013 | Vengco |
| 2014/0214450 A1 | 7/2014 | Bechtold et al. |
| 2014/0244300 A1 | 8/2014 | Bess et al. |
| 2014/0324476 A1 | 10/2014 | Dufel et al. |
| 2015/0180707 A1* | 6/2015 | Canessa ............. H04L 41/5064 709/217 |

* cited by examiner

ELECTRONIC MEDICAL RECORD EXCHANGE

CROSS REFERENCE TO RELATED APPLICATIONS

This application is a continuation of U.S. application Ser. No. 12/893,384 filed Sep. 29, 2010, the disclosures of which are hereby incorporated by reference as if fully restated herein.

FIELD OF THE INVENTION

This invention relates generally to electronic medical records. More particularly, this invention relates to an electronic medical record exchange system to provide universal message exchange between disparate legacy electronic medical record systems.

BACKGROUND OF THE INVENTION

An electronic medical record is a collection of health information in electronic form. The health information may relate to an individual's medical history, medications consumed, allergies, immunization status, laboratory test results, radiology images, billing information and the like. An electronic medical record (EMR) is sometimes referred to as an electronic health record (EHR), electronic patient record (EPR) or computerized patient record.

EMRs are used to facilitate the automation and streamlining of the workflow in health care settings. In addition, it is a goal to use EMRs to improve healthcare through evidence-based decision support, quality management and outcome reporting. While this is a laudable goal, it remains elusive in view of the capital costs, training costs and maintenance costs of new systems.

Legacy systems are typically incompatible with one another. For example, a physician's office may have a first legacy system that is incompatible with a second legacy system at a hospital. Consequently, a doctor that works at both the physician's office and the hospital may not be able to exchange records between these two venues. In other words, the doctor may be able to use the first legacy system at the physician's office and the second legacy system at the hospital, but the two systems operate in separate silos and are otherwise not integrated.

A central data server may be used to store the different records, but this represents an entirely new system with significant capital costs. In addition, there are challenges associated with normalizing disparate records and then loading them into a single repository. This solution also raises confidentiality concerns.

It is desirable to allow health care professionals to continue to use their legacy systems. However, it is also desirable to integrate such legacy systems with other legacy systems that have incompatible formats. For an integration to be practical, it must be relatively inexpensive. In addition, it must overcome challenges related to disparate doctor identifiers and patient identifiers used in the different systems. Further, it must support message exchanges between legacy systems that require different message formats. In addition, such a solution should provide a comprehensive audit trail of messages that traverse between legacy systems.

SUMMARY OF THE INVENTION

An electronic medical record exchange system includes an electronic medical record appliance to interface with a first legacy electronic medical record system. An electronic medical record gateway server interfaces with the electronic medical record appliance and a second legacy electronic medical record system. The electronic medical record appliance and the electronic medical record gateway server communicate utilizing assigned doctor identifiers and patient identifiers that are different than assigned doctor identifiers and patient identifiers utilized by the first legacy electronic medical record system and the second legacy electronic medical record system.

BRIEF DESCRIPTION OF THE FIGURES

The invention is more fully appreciated in connection with the following detailed description taken in conjunction with the accompanying drawings, in which.

Like reference numerals refer to corresponding parts throughout the several views of the drawings.

DETAILED DESCRIPTION OF THE INVENTION

Figure 1:
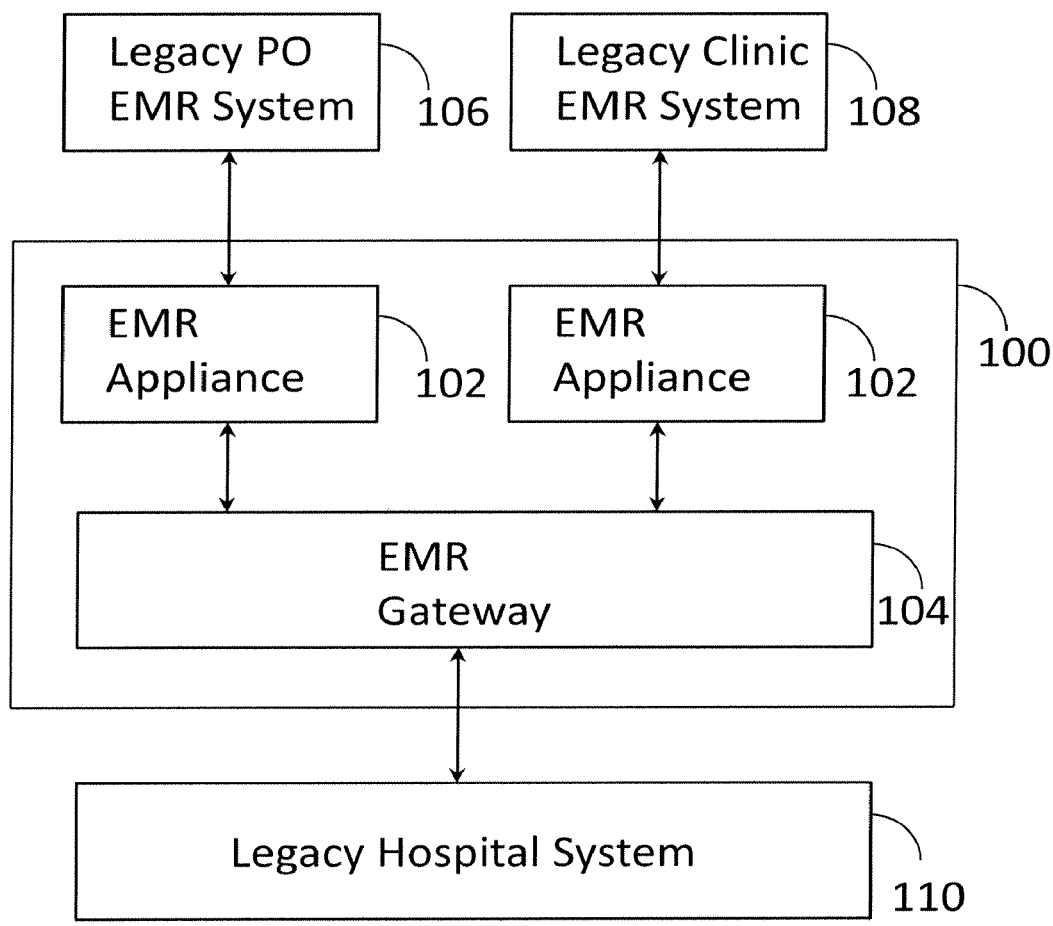
FIG. 1 illustrates an electronic medical record exchange system configured in accordance with an embodiment of the invention.

FIG. 1 illustrates an electronic medical record (EMR) exchange system 100 configured in accordance with an embodiment of the invention. The system 100 includes a set of EMR appliances 102. Each EMR appliance 102 is a hardware platform designed to provide an EMR computing resource. An appliance is a closed and sealed system that is not serviceable by a user. Thus, it stands in contrast to a general purpose computer, where a user can modify the hardware configuration and load any type of software desired. An appliance has a limited interface, usually a terminal console or web-based, to allow limited configuration operations. The EMR appliance is desirable because it effectively runs on its own, thereby reducing IT expenses. Automated back-up, software control and maintenance are done behind the scenes, eliminating headaches like software installation, conflicts and updates. The EMR appliance also provides protection from viruses, hackers or other threats to security. Thus, the EMR appliance reduces initial capital costs and ongoing maintenance costs.

Each EMR appliance 102 is connected to an EMR gateway server 104. The EMR gateway server 104 is a general purpose computer implementing operations of the invention. The EMR appliances 102 and EMR gateway server 104 operate as an EMR exchange system 100 to provide interoperability with legacy EMR systems. For example, a first EMR appliance may be connected to a legacy physician's office EMR system 106, while another EMR appliance 102 may be connected to a legacy medical clinic EMR system 108. The EMR gateway server 104 may be connected to a legacy hospital EMR system. In general, an EMR appliance 102 is used in connection with a relatively small legacy EMR system, while an EMR gateway 104 is used in connection with a relatively large legacy EMR system. The system 100 may be configured with additional EMR appliances and EMR gateways 104.

The EMR exchange system 100 uses its internal components (102, 104) to communicate in a domain with common doctor and patient identifiers that are different than the doctor and patient identifiers utilized in the legacy EMR systems. The EMR exchange system 100 also provides an end-to-end audit trail of messages exchanged between legacy EMR systems. In addition, the EMR exchange system 100 transforms incompatible message formats utilized by different EMR legacy systems to provide compatibility between the different EMR legacy systems.

Figure 2:
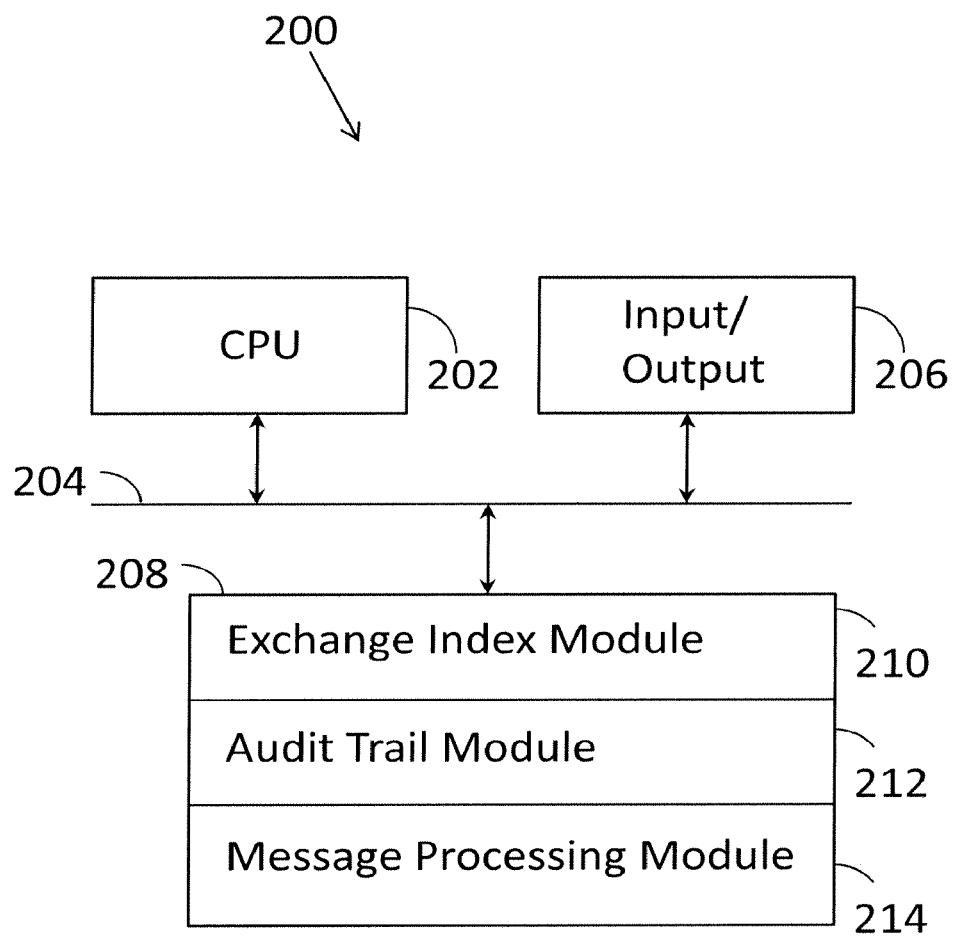
FIG. 2 illustrates an appliance or gateway configured in accordance with an embodiment of the invention.

FIG. 2 illustrates a computation device 200 configured in accordance with an embodiment of the invention. The computation device 200 may be configured as an EMR appliance 102 or an EMR gateway server 104. In the case of an EMR gateway server 104, standard server components are used, such as a central processing unit 202 and input/output devices 206 connected by a bus. The input/output devices 206 may include a keyboard, mouse, display, printer and the like. A memory 208 is also connected to the bus. The memory 208 includes executable instructions to implement operations of the invention. In one embodiment, the memory 208 includes an exchange index module 210. The exchange index module 210 includes executable instructions to assign doctor and patient identifiers that are used within the EMR exchange system 100. This allows the EMR exchange system 100 to efficiently identify and process doctor and patient records within the system 100, while still being compatible with legacy systems that use different doctor and patient identifiers.

The memory 208 also includes an audit trail module 212. The audit trail module 212 includes executable instructions to provide end-to-end tracking of a message passed through the EMR exchange 100, as discussed below.

The memory 208 also includes a message processing module 214. The message processing module 214 includes executable instructions to transform incompatible message formats from different legacy systems into a format that can be used by different legacy systems, as discussed below.

The operations of modules 210, 212 and 214 are also implemented in each EMR appliance 102. Thus, an EMR appliance 102 may have a similar configuration to device 200. However, the appliance 102 will typically omit the input/output devices 206. Further, the appliance 102 may implement its operations through an Application Specific Integrated Circuit or other custom hardware instead of a general purpose central processing unit. Regardless of the appliance configuration, it operates in conjunction with the EMR gateway 104 to provide patient and doctor identifiers, audit trail tracking and message processing. These operations are distributed between an EMR appliance 102 and an EMR gateway 104, as discussed below.

Figure 3:
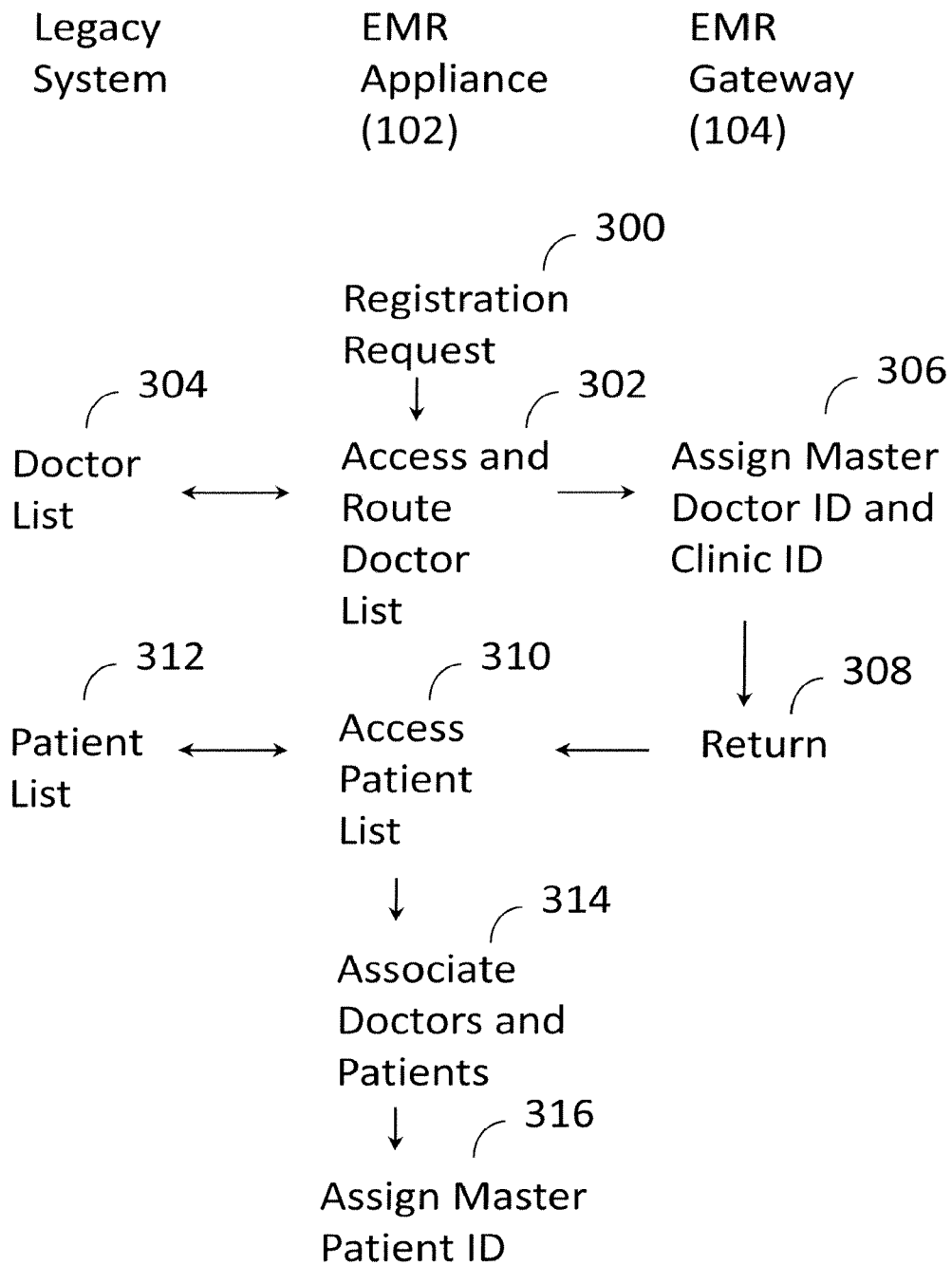
FIG. 3 illustrates the establishment of master indices in accordance with an embodiment of the invention.

FIG. 3 illustrates operations associated with assigning master doctor and patient identifiers in accordance with an embodiment of the invention. The figure illustrates operations performed across various machines, including a legacy system, an EMR appliance 102 and an EMR gateway 104.

A legacy system, such as a system at a hospital or a clinic, includes a physician and patient database. The identifier for a patient or a physician at one legacy system (e.g., a hospital) could be different than the identifier at another legacy system (e.g., a clinic).

When the EMR appliance 102 is initially activated, it generates a registration request 300. The registration request 300 initiates an access to a list of doctors 304 in a legacy system. The list of doctors is then routed 302 to the EMR gateway 104. The EMR gateway 104 assigns a master doctor identifier to each doctor on the list. This master doctor identifier is used within the medical record exchange system 100. A clinic identifier may also be assigned to the doctor so that a doctor operating at different clinics can be uniquely identified and coordinated with appropriate patients. The master doctor identifier is then returned 308 to the EMR appliance 102. This causes the EMR appliance 102 to access 310 a patient list 312 within the legacy system. The EMR appliance 102 associates doctors and patient 314. Thereafter, the EMR appliance 102 assigns master patient identifiers 316 to each patient. Each master patient identifier is used within the EMR exchange system 100. Each master patient identifier is typically different than the patient identifier used in the legacy system.

From this point forward, any received EMR can be mapped from a legacy system identifier to a master identifier utilized within the EMR exchange system 100. For example, an EMR message utilizing the doctor identifier and patient identifier of legacy Physician Office EMR system 106 is mapped to the master doctor identifier and master patient identifier of the electronic medical record exchange system 100. The master doctor identifier and/or master patient identifier may then be mapped to a doctor or patient at legacy clinic EMR system 108.

Each master identifier is a unique value that has an associated list of values for legacy systems. For example, the master doctor identifier has a unique value. This unique value is associated with a list of doctor identifiers used for the same doctor at different offices, clinics, or hospitals. The same approach is used with the master patient identifier. The term "master" indicates a prevailing identifier in the electronic medical record exchange systems 100. However, it is not a "master" identifier across an entire EMR system. The use of a single "master" identifier across an entire EMR system implies centralized control, which is expensive and otherwise meets resistance for a variety of reasons. In contrast, the invention provides a distributed system that allows incompatible legacy systems to operate with one another.

If a message is received at the gateway 104, it is routed to an appliance 102 associated with a clinic or office that the doctor practices at. In other words, the message is routed in accordance with the master doctor identifier and clinic identifier. The appliance 102 can then link the master patient identifier with the patient identifier used by the legacy system. Consequently, the EMR exchange system 100 provides interoperability between legacy systems without synchronization between different databases.

Figure 4:
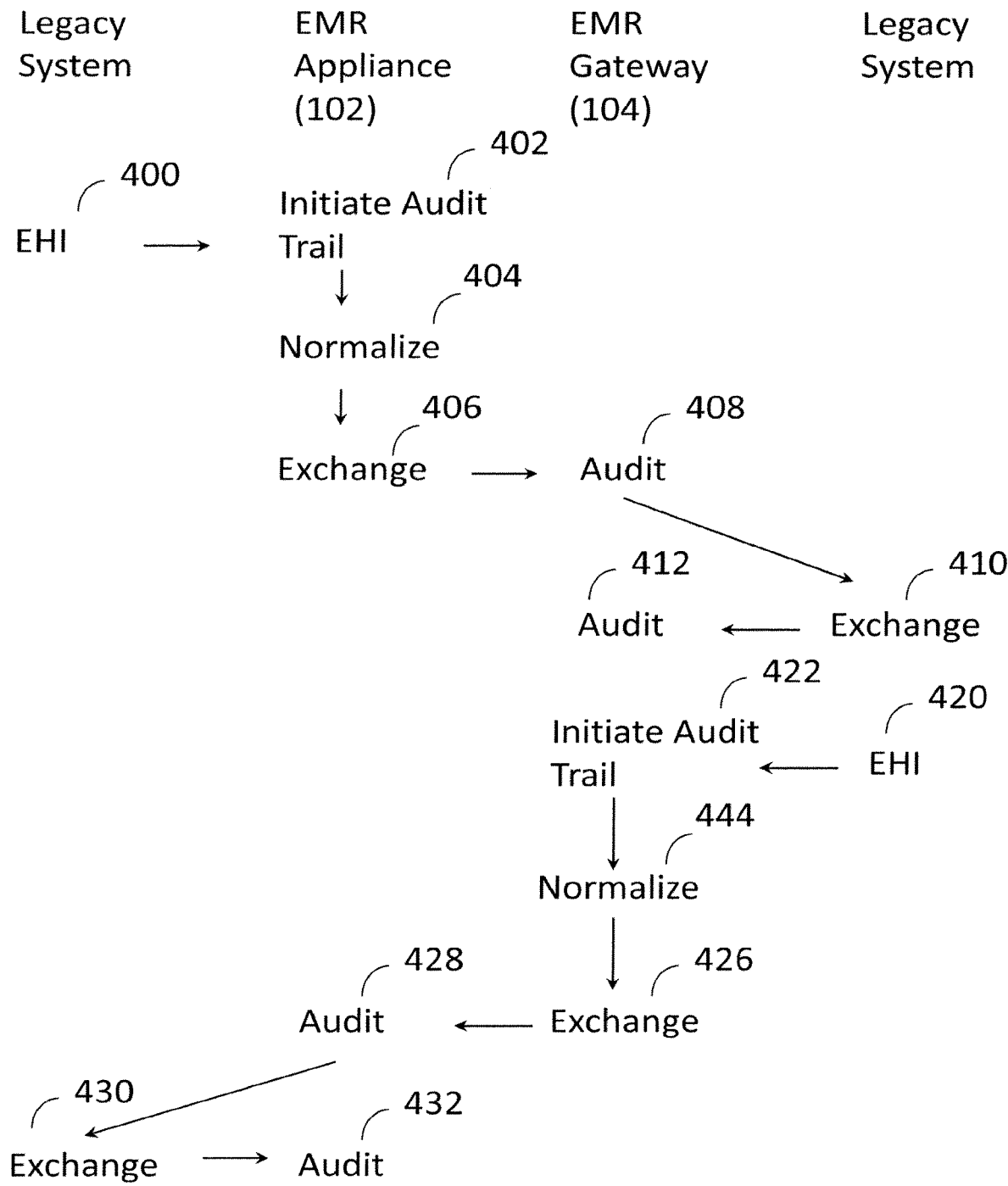
FIG. 4 illustrates record audit trail and normalization operations performed in accordance with an embodiment of the invention.

FIG. 4 illustrates audit trail processing performed in accordance with an embodiment of the invention. For example, a legacy system generates electronic health information (EHI) 400, which is passed to the EMR appliance 102. The electronic health information may be in form of an EMR. Receipt of the EHI at the EMR appliance 102 initiates an audit trail 402. Optionally, the message may be normalized 404 for compatibility with another legacy system. That is, a sender (e.g., a hospital) and a receiver (e.g., a clinic) may require different message formats. The sender and receiver can ignore these incompatibilities since they are handled by the EMR exchange system 100. The EMR appliance 102 or the EMR gateway 104 identifies the target system and then evaluates data conformance rules utilized by the target system. For example, a sent message may be in HL7 2.3 form. However, the recipient requires a 2.5 format.

In this case, the appliance 102 invokes a script to convert the message from 2.3 to 2.5 before passing it on. Alternately, an HL7 message may have an outpatient code of "OP". The receiving system may require a single character outpatient code. The appliance 102 utilizes a script to provide the appropriate format. Alternately, a message may have a segment unrecognized by the target system. In this case, the appliance deletes such a segment so that it can be processed at the target system.

After any required normalization, the message is then exchanged 406 with the EMR gateway 104. The message is audited 408 at the EMR gateway 104. At this point, the message would typically be directed toward another legacy system through another exchange 410. An acknowledgement from the legacy system may then be audited 412.

Alternately, an EHI 420 may be generated at another legacy system and be initially passed to the EMR gateway 104. In this case, the EMR gateway 104 initiates an audit trail 422. If necessary, the message is normalized 444. The message is then exchanged 426 to the EMR appliance 102, where it is audited 428. The message is then exchanged 430 to another legacy system. An acknowledgement from the legacy system may then be audited 432.

The audit trail allows for the tracking of the progress of messages. The audit trail can be used to certify that a message was properly acknowledged by a target receiving entity. The appliance 102 and gateway 104 may keep separate audit trails. Alternately, their audit trail information may be exchanged to produce comprehensive audit trail information.

The system generates a unique message identifier for each outgoing message. One message may be sent to several recipients. As a result, there is a 1-to-N mapping from an outgoing message identifier to an incoming message identifier. The unique identifier of the incoming message is associated with the outgoing message identifier for correlation.

An incoming message may not result in an outgoing message. In this case, a doctor identifier and clinic identifier may be used for audit purposes. A legacy system may require a doctor to be of a fixed type (e.g., attending physician) to receive a message. The EMR exchange system 100 may transform a doctor to a fixed type (e.g., from referring to attending) to enable receipt of a message. The audit trail may be used to preserve the original doctor type.

Figure 5:
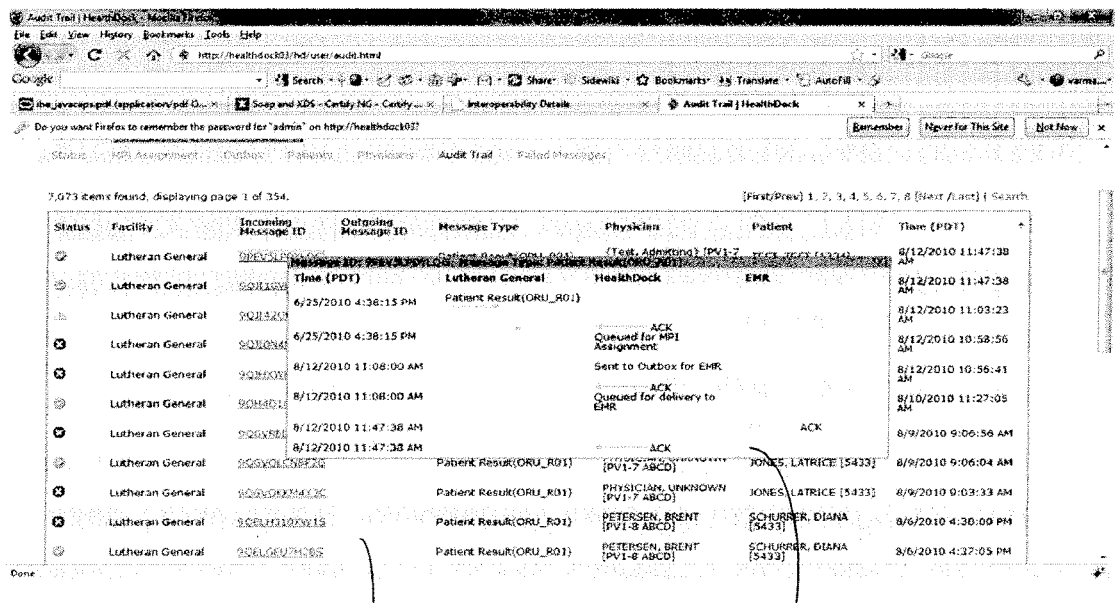
FIG. 5 illustrates a record audit trail supplied in accordance with an embodiment of the invention.

FIG. 5 illustrates an audit trail formed in accordance with an embodiment of the invention. Window 500 displays message information, including status information, incoming message ID, outgoing message ID, message type, physician, patient and time. Window 502 illustrates tracking of an individual message. In this example, a patient result is generated by a legacy system (Lutheran General) and is passed to EMR appliance 102 (Healthdock). The message is queued and then sent to the associated clinic legacy system (EMR). The receipt of the message is then acknowledged by the legacy system.

Figure 6:
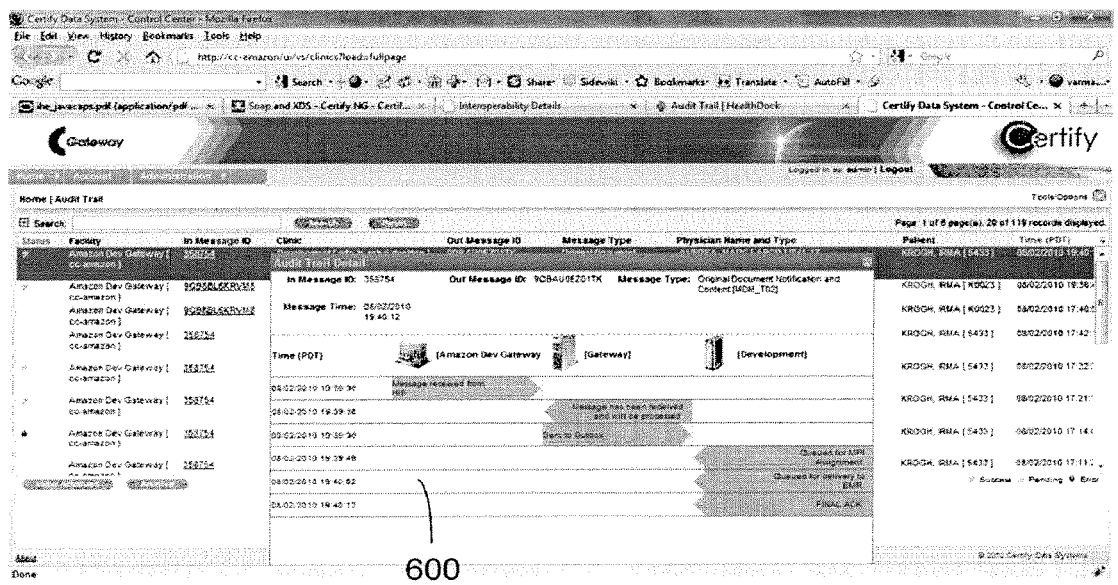
FIG. 6 illustrates a record audit trail supplied in accordance with another embodiment of the invention.

FIG. 6 illustrates a window with an audit trail that uses different shading or coloring to represent the status of a message. For example, one shade may be used for receipt of a message, another for queuing a message, another for sending a message, another for an initial acknowledgment and another for a final acknowledgment.

An embodiment of the present invention relates to a computer storage product with a computer readable storage medium having computer code thereon for performing various computer-implemented operations. The media and computer code may be those specially designed and constructed for the purposes of the present invention, or they may be of the kind well known and available to those having skill in the computer software arts. Examples of computer-readable media include, but are not limited to: magnetic media such as hard disks, floppy disks, and magnetic tape; optical media such as CD-ROMs, DVDs and holographic devices; magneto-optical media; and hardware devices that are specially configured to store and execute program code, such as application-specific integrated circuits ("ASICs"), programmable logic devices ("PLDs") and ROM and RAM devices. Examples of computer code include machine code, such as produced by a compiler, and files containing higher-level code that are executed by a computer using an interpreter. For example, an embodiment of the invention may be implemented using JAVA®, C++, or other object-oriented programming language and development tools. Another embodiment of the invention may be implemented in hard-wired circuitry in place of, or in combination with, machine-executable software instructions.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, they thereby enable others skilled in the art to best utilize the invention and various embodiments with various modifications as are suited to the particular use contemplated. It is intended that the following claims and their equivalents define the scope of the invention.

What is claimed is:

1. A system for providing compatibility between legacy electronic medical record (EMR) systems, said system comprising:
 a first appliance in ongoing two-way electronic communication with a first legacy EMR system on an on-demand basis and configured to convert medical records data between a first format utilized by the first legacy EMR system and a common format for transmission to a third legacy EMR system;
 a second appliance in ongoing two-way electronic communication with a second legacy EMR system on an on-demand basis and configured to convert medical records data between a second format utilized by the second legacy EMR system and the common format for transmission to a third legacy EMR system;
 a common gateway server in ongoing two-way electronic communication with the first appliance, the second appliance, and a third legacy EMR system on an on-demand basis, wherein said common appliance is configured to convert medical records data between a third format utilized by the third legacy EMR system and the common format for transmission from the third legacy EMR system to the first or second legacy EMR system by way of the first or second appliance, respectively, for integration with the medical records data of said first or second legacy EMR system or for transmission to the third EMR system from the third or second legacy EMR system for integration into the medical records data of the third legacy EMR system; and a closed network comprising the first appliance, the second appliance, and the common gateway server;

wherein each of said first, second, and third legacy EMR systems comprise a number of legacy doctor identifiers and a number of legacy patient identifiers, wherein each of said number of legacy patient identifiers are associated with at least one of said number of legacy doctor identifiers;

wherein each of said first appliance, said second appliance, and said common gateway server are configured to associate a received one of the number of legacy patient identifiers with a closed network patient identifier, and associate a received one of the number of legacy doctor identifiers with a closed network doctor identifier, prior to transmitting said medical records data between any of said first appliance, said second appliance and said common gateway server; and wherein said first appliance, said second appliance, and said common gateway server are each configured to associate the received closed network patient identifier with the corresponding legacy patient identifier, and associate the received closed network doctor identifier with the corresponding legacy doctor identifier, following receipt of the patient medical records data from another one of the first appliance, the second appliance, and the common gateway server and prior to transmitting said patient medical records to a respective one of the first, second, and third legacy EMR systems.

2. The system of claim 1 wherein:

each of said closed network patient identifiers is different than each of the patient identifiers; and each of said closed network doctor identifiers is different than each of the doctor identifiers.

3. The system of claim 2 wherein:

each of said first appliance, the second appliance, and the common gateway server are configured to accept a registration request, assign a new doctor identifier, assign a new closed network doctor identifier, associate the new closed network doctor identifier with the new doctor identifier, assign at least one new patient identifier, assign at least one new closed network patient identifier, and associate the new closed network patient identifier with the patient identifier.

4. The system of claim 1 wherein:

each of the first appliance, second appliance, and said common gateway server have a limited interface that inhibits user inputted operation after setup.

5. The system of claim 4 wherein:

each of said first appliance, said second appliance, and said common gateway server are dedicated, closed, and sealed systems.

6. The system of claim 1 wherein:

the closed network is operative with the first, second, and third legacy EMR systems without synchronization of databases between the first, second, and third legacy EMR systems.

7. The system of claim 1 wherein:

each of the first appliance, said second appliance, and said common gateway server are configured to maintain an audit trail of medical records data exchanged between any of the first, second, and third legacy EMR systems and the first appliance, the second appliance, and the common gateway server.

8. The system of claim 7 wherein:

each of the first appliance, the second appliance, and the common gateway server are configured to maintain the audit trail of medical records data exchanged between any of the first, second, and third legacy EMR systems and the first appliance, the second appliance, and the common gateway server by generating and assigning a unique message identifier to each transmission and receipt of medical records data.

9. The system of claim 1 wherein:

each of said first appliance, the second appliance, and the common gateway server are in direct electronic communication with only a respective one of the first, second, and third legacy EMR systems.

\* \* \* \* \*